United States Patent [19]
Shichman et al.

[11] Patent Number: 5,322,161
[45] Date of Patent: Jun. 21, 1994

[54] CLEAR PACKAGE FOR BIOABSORBABLE ARTICLES

[75] Inventors: Daniel Shichman, Trumbull; David L. Brown, Wallingford; Stanley J. Malinowski, Guilford, all of Conn.

[73] Assignee: United States Surgical Corporation, Norwalk, Conn.

[21] Appl. No.: 982,825

[22] Filed: Nov. 30, 1992

[51] Int. Cl.$^5$ ............................................. B65D 81/26
[52] U.S. Cl. ..................................... 206/204; 53/428; 206/363
[58] Field of Search ................. 53/400, 425, 426, 428, 53/455; 206/204, 205, 328, 339, 340, 363, 364, 438, 439, 484, 484.1

[56] References Cited

U.S. PATENT DOCUMENTS

| | | |
|---|---|---|
| 3,256,981 | 6/1966 | Kurtz . |
| 3,301,788 | 1/1967 | Cummings et al. . |
| 3,326,810 | 6/1967 | Dolan et al. . |
| 3,442,686 | 5/1969 | Jones . |
| 3,728,839 | 4/1973 | Glick . |
| 4,036,360 | 7/1977 | Deffeyes . |
| 4,135,622 | 1/1979 | Glick . |
| 4,511,035 | 4/1985 | Alpern ........................... 206/363 |
| 4,528,234 | 7/1985 | Kaiho et al. . |
| 4,702,963 | 10/1987 | Phillips et al. . |
| 4,730,726 | 3/1988 | Holzwarth ..................... 206/204 |
| 4,852,732 | 8/1989 | Wilski et al. ................... 206/204 |
| 4,971,196 | 11/1990 | Kitamura et al. ............... 206/204 |
| 5,084,356 | 1/1992 | Deak et al. . |
| 5,129,511 | 7/1992 | Brown et al. . |

FOREIGN PATENT DOCUMENTS

| | | | |
|---|---|---|---|
| 0293321 | 8/1991 | Fed. Rep. of Germany | 206/204 |
| 2660634 | 10/1991 | France | 206/204 |
| 0711186 | 6/1954 | United Kingdom | 206/204 |

OTHER PUBLICATIONS

Rollprint Packaging Products, Inc. (Addison, Illinois) information sheet for Clear Foil TM I (CPET).
Information Booklets for Polysorb staples and Poly Surgiclip clip appliers packaged in foil laminate packages containing a desiccant pouch.

*Primary Examiner*—Jimmy G. Foster

[57] ABSTRACT

A flexible package of low moisture permeability suitable for packaging moisture sensitive materials and devices such as bioabsorbable surgical staples and clips and instruments containing these devices includes a first panel fabricated from a substantially transparent polymeric laminate film possessing an inorganic moisture vapor transmission barrier layer, the first panel having a measurable moisture vapor transmission rate and being bonded along its edges to the edges of a second panel fabricated from either (i) a transparent flexible polymeric laminate film possessing an inorganic moisture vapor transmission barrier layer which is the same as, or is different from, the film of the first panel; or (ii) an opaque, flexible metal foil laminate to form a contents-enclosing pouch therebetween, the pouch containing a quantity of desiccant and at least one sterile moisture-sensitive material or device, e.g., the aforesaid bioabsorbable staples, clips or instruments containing such staples or clips.

42 Claims, 3 Drawing Sheets

CLEAR PACKAGE FOR BIOABSORBABLE ARTICLES

BACKGROUND OF THE INVENTION

The present invention relates to a package for synthetic bioabsorbable surgical articles and, more particularly, to such a package which is at least partially transparent for product visibility. More particularly, the invention relates to a package in which a first panel fabricated from a transparent, flexible polymeric laminate film possessing an inorganic moisture vapor transmission barrier layer is bonded along its edges to the edges of a second panel fabricated from a transparent, flexible polymeric film possessing an inorganic moisture vapor transmission barrier layer or from a moisture impermeable, opaque, flexible metal foil laminate to form a contents-enclosing pouch therebetween, the pouch containing a quantity of desiccant therein. This arrangement permits the contents of the package to be viewed without having to first open the package, an event which would only compromise the sterility of the contents.

The packaging of moisture-sensitive materials, devices, etc., in flexible packages manufactured in their entirety from metal foil laminate is universally practiced. Packages of this kind are widely used for the packaging of polymeric absorbable surgical clips and staples which are prone to degradation resulting from prolonged contact with moisture. Metal foil laminates have an immeasurably low water vapor transmission rate and provide a complete barrier to water vapor transmission which has heretofore been believed necessary for packaging polymeric absorbable products. Unfortunately, however, metal foil laminates are necessarily opaque and as a result, a package made from such laminates does not permit visual identification or inspection of its contents without being opened.

U.S. Pat. No. 3,256,981 describes a flexible package for sutures possessing a metal foil laminate as one of its sides and a transparent film of a polytrifluoroethylene film exhibiting a low water vapor transmission rate (Allied Chemical Company's Aclar ® film) as the other. This package has not been accepted for the packaging of bioabsorbable surgical devices to protect such devices from moisture-induced degradation over extended periods. Indeed, prior to the present invention, it was generally accepted that foil laminate packaging was the only suitable packaging for synthetic absorbable articles and that moisture pervious packages such as described in U.S. Pat. No. 3,256,981 were incapable of adequately protecting such articles. The high cost of the polytrifluoroethylene film used in the construction of the package of U.S. Pat. No. 3,256,981 is believed to have been an additional factor further discouraging its use for the packaging of synthetic absorbable articles.

Transparent films useful for the construction of flexible packages possessing low water vapor transmission rates but avoiding the high cost of a polytrifluoroethylene film are known from, among others, U.S. Pat. Nos. 3,442,686, 4,528,244, 4,702,963 and 5,084,356.

U.S. Pat. No. 3,442,686 describes a transparent, flexible packaging film laminate consisting of a polymeric base sheet such as polyethylene terephthalate film having a heat-sealable top coating of a film-forming polymer such as polyethylene and an intermediate gas and liquid barrier layer of an inorganic material such as a silicon oxide.

The flexible packaging film of U.S. Pat. No. 4,528,234 includes a polymeric base film or sheet, a thin layer of at least one metal such as aluminum, tin, iron, zinc or magnesium formed on the base film or sheet by vacuum deposition or sputtering and a carboxyl group-containing polyolefin layer formed on the metal layer by lamination.

U.S. Pat. No. 4,702,963 describes a transparent, flexible packaging film possessing a thin layer of chromium formed on a polymeric film substrate layer and a thin layer of a glass material, e.g., a silicon oxide, formed on the chromium layer.

U.S. Pat. No. 5,085,356 discloses a transparent, flexible packaging film in which a glassy coating of silicon dioxide heavily doped with at least one of antimony, aluminum, chromium, cobalt, copper, indium, iron, lead, manganese, tin, titanium, tungsten, zinc or zirconium is applied to a polymeric film substrate.

A common strategy for dealing with moisture which may have penetrated a sealed package containing moisture sensitive goods is to insert a desiccant within the package. Known desiccant materials and desiccant units include molecular sieves such as zeolite Z-12 (U.S. Pat. No. 3,301,788), silica gel packaged between two sheets of nylon mesh bonded with a microporous polyurethane (U.S. Pat. No. 3,326,810) and a desiccant material such as alumina, bauxite, anhydrous calcium sulfate, water-absorbing clay, zeolite, or the like, optionally including a moisture sensitive color indicator such as cobalt chloride to indicate when the desiccant is "used up", in a binder of prepolymerized polyurethane resin (U.S. Pat. No. 4,036,360).

SUMMARY OF THE INVENTION

It is an object of the invention to provide an at least partially transparent flexible package of low water vapor transmission characteristics for packaging moisture sensitive contents.

It is a particular object of the invention to provide such a package manufactured from a first, or front, panel fabricated from a relatively low cost transparent, flexible polymeric film laminate of low moisture vapor transmission rate and a second, or rear, panel fabricated from a transparent, flexible polymeric film laminate of low moisture vapor transmission rate which may or may not be identical with that of the first panel or from a moisture impermeable, opaque, flexible metal foil laminate, e.g., one of aluminum, the package containing a quantity of desiccant therein.

It is a further particular object of the invention to provide an at least partially transparent flexible package for the packaging of surgical devices, e.g., staples and clips, formed from bioabsorbable synthetic polymers such as homopolymers and copolymers of glycolide, glycolic acid, lactide, lactic acid, p-dioxanone, epsilon-caprolactone, etc., and surgical instruments such as staplers and clip appliers containing such devices. Unlike the foil laminate packages which heretofore have been used to package such devices, the package of the present invention including at least one transparent, flexible polymeric film laminate layer is not moisture impervious but, rather, possesses a distinct and measurable moisture vapor transmission rate. The foil laminates which have heretofore been used for packaging such articles do not possess a measurable moisture vapor transmission rate.

By way of meeting the foregoing and other objects of the invention, there is provided a flexible package comprising a first panel fabricated from a substantially transparent flexible polymeric laminate film possessing an inorganic moisture vapor transmission barrier layer, said first panel having a measurable moisture vapor transmission rate, the first panel being bonded along its edges to the edges of a second panel fabricated from a material selected from the group consisting of (i) a transparent flexible polymeric laminate film possessing an inorganic moisture vapor transmission barrier layer which is the same as, or is different from, the film of the first panel and (ii) an opaque, flexible metal foil laminate, to form a contents-enclosing pouch therebetween, the pouch containing a quantity of desiccant and a bioabsorbable polymeric surgical device.

While it has heretofore been considered inappropriate to package synthetic absorbable articles in the moisture pervious package of U.S. Pat. No. 3,251,981, the package of this invention is suitable for packaging moisture sensitive materials, articles, devices, etc., and is particularly useful for the long term packaging (e.g., up to 24 months or longer) of bioabsorbable surgical devices such as the previously mentioned staples and clips and surgical instruments containing such devices. Unlike the relatively expensive transparent polytrifluoroethylene film component of the package disclosed in U.S. Pat. No. 3,251,981 the polymeric laminate film component of the package herein is comparatively low in cost.

DESCRIPTION OF THE PREFERRED EMBODIMENTS

Figure 1:
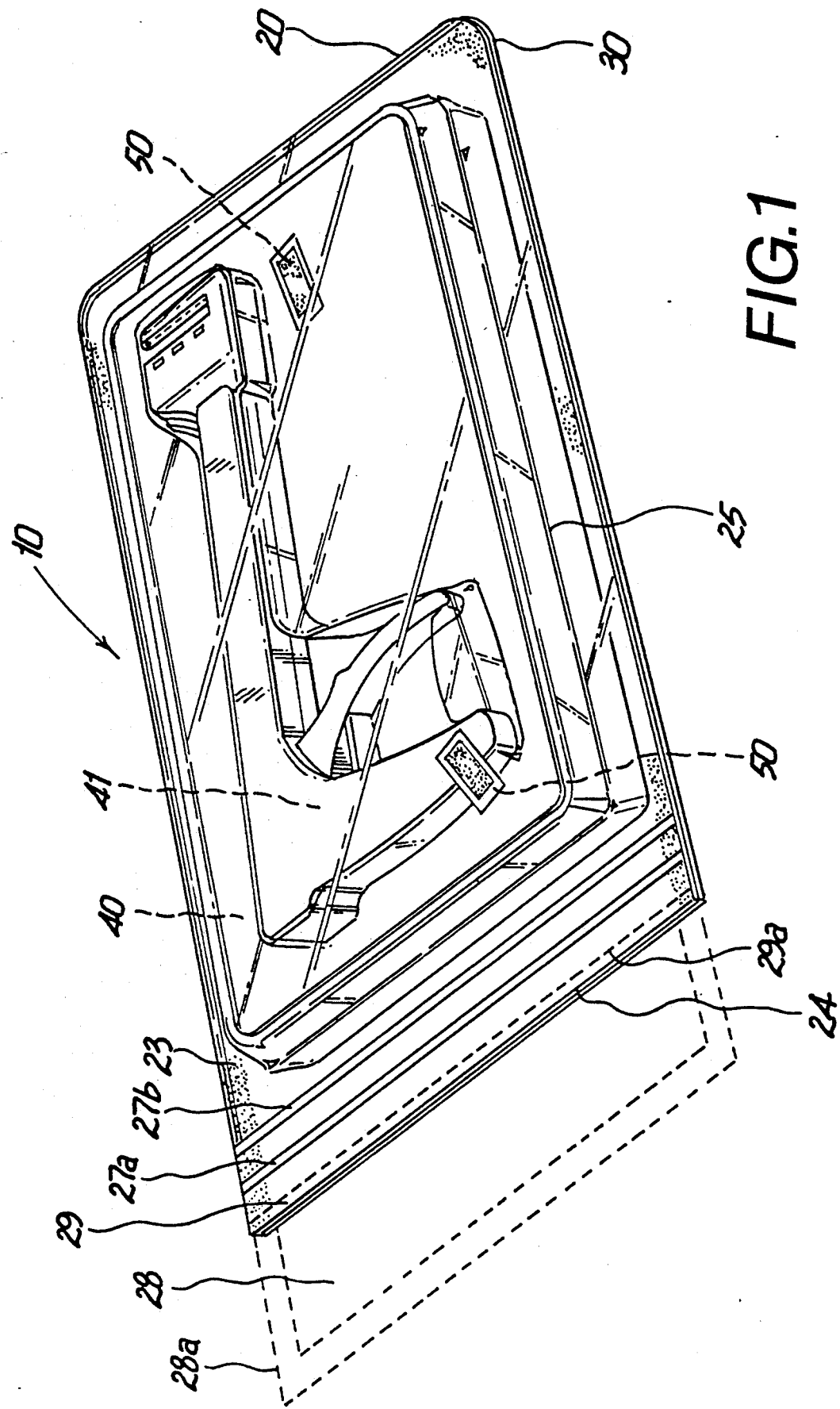
FIG. 1 is a perspective view of a package of this invention with its header portion still attached, the pouch enclosing a transparent, rigid inner tray package containing a surgical stapler instrument loaded with a quantity of bioabsorbable surgical staples.
Figure 2:
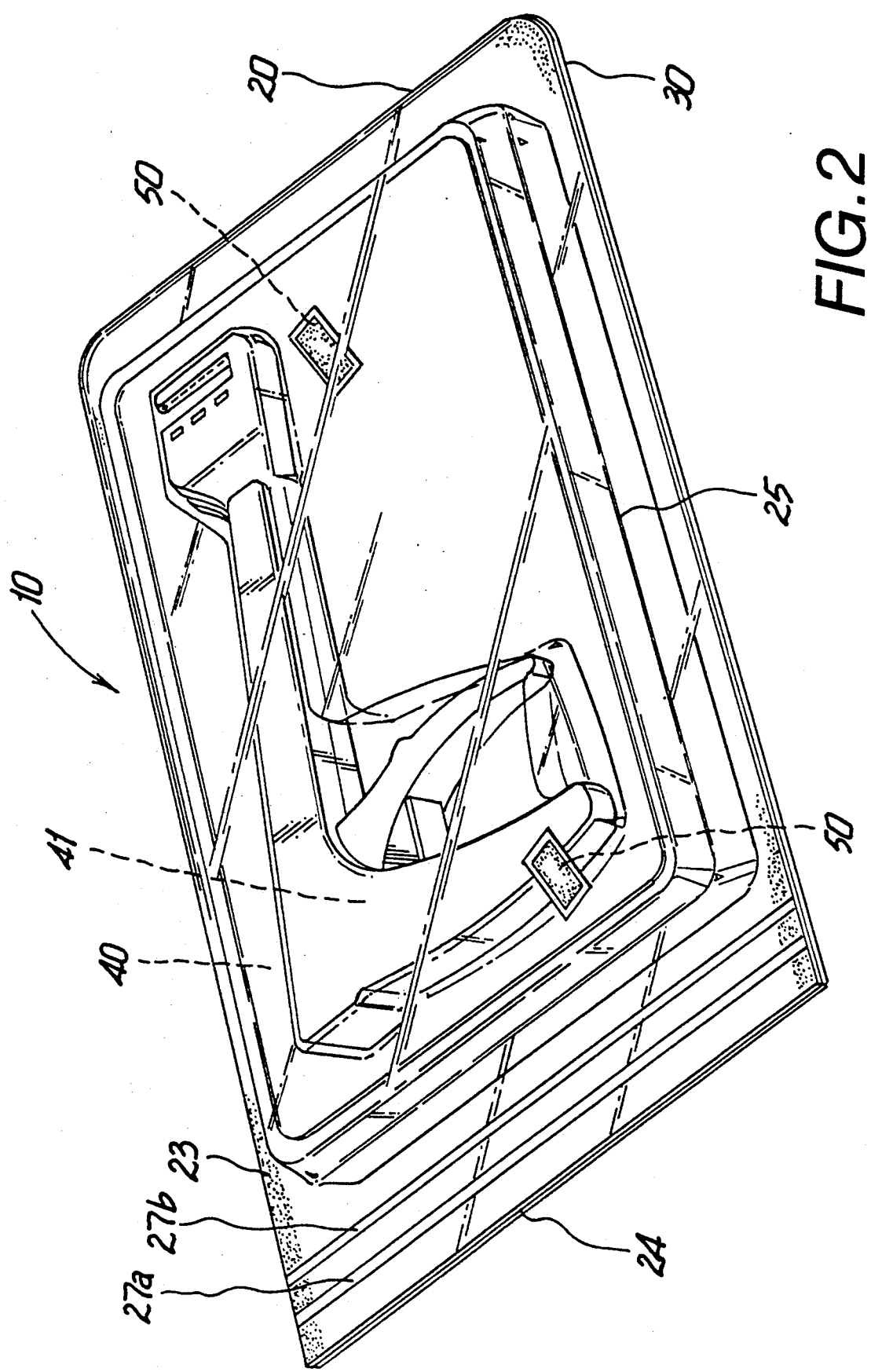
FIG. 2 is a perspective view of the fully sealed package of FIG. 1 with the header removed.

As shown in FIGS. 1 and 2, fully sealed flexible package 10 is constructed from a generally rectangular first, front, or viewing panel 20 adhesively bonded along its edges to the edges of a similarly configured second, or rear, panel 30. The space between panels 20 and 30 defines a pouch 25 which is occupied by a transparent, rigid, vacuum-formed inner tray package 40 containing a surgical stapler instrument 41 whose staple storage magazine is loaded with a quantity of absorbable staples made from glycolide-lactide copolymer. Surgical stapler instruments of this type are described, e.g., in U.S. Pat. Nos. 4,523,591, 4,744,365 and 4,844,854.

Prior to insertion of inner tray package 40 and one or more desiccant units 50 into pouch 25 of package 10, panel 30 possesses an extension 28, indicated in dotted outline, which with coterminous overlying sheet 20 forms header 28a. Extension 28 is fabricated from a sheet material which is gas permeable but serves as a barrier to microorganisms. A suitable material of this type is Tyvek, Du Pont's spunbonded polyethylene. A portion of extension 28 overlaps, and is adhesively secured to, the underside of panel 30 where it defines a strip portion 29, margin 29a of which is indicated in dotted outline in FIG. 1. In this initial, or presealing, condition of the package, inner tray package 40 with its loaded surgical stapler instrument 41 and at least one desiccant unit 50 are inserted into pouch 25. The open edges of header 28a are then sealed to completely secure package 10 against entry of microorganisms. The package is then placed in a sterilization gas atmosphere, e.g., one containing ethylene oxide, the gas entering the package through the Tyvek side of header 28a where it sterilizes the contents of pouch 25. Following an appropriate period of sterilization and aeration to remove the sterilization gas from the interior of package 10, panel 20 is bonded to panel 30 forming double seal strips 27a and 27b. Finally, extension 28 with header 28a attached thereto is removed in a cutting operation thereby forming edge 24 of the completely sealed and interiorly sterile package of FIG. 2. The separation of extension 28/header 28a can be effected outside or within margin 29a of the header. When accomplished outside margin 29a, the header material will be completely removed from the filled, sealed and sterilized package. However, if separation of extension 28/header 28a is accomplished by a cut formed within margin 28a of the header, strip portion 29 constituting the residue of the header will remain attached to the package.

Figure 5:
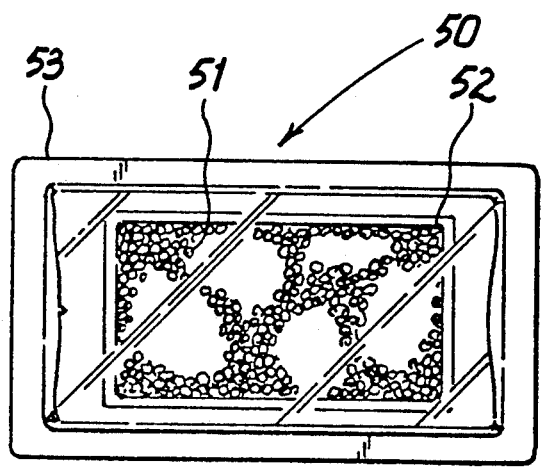

Desiccant units 50, described more fully below in connection with FIG. 5, are included in pouch 25 to absorb any moisture which may penetrate package 10 over time. The desiccant units can be loosely placed within pouch 25 where they can shift about with movement of the package or, preferably, they can be adhesively bonded to an interior surface of the pouch, advantageously second panel 30, so as to remain in fixed locations however the package may be handled.

The shape and dimensions of a package constructed in accordance with the invention will, of course, depend upon the particular packaging application. In the specific case of package 10, pouch dimensions are approximately 17 by 9 inches with pouch dimensions measuring approximately 16.6 by 8 inches. The overall average thickness of panels 20 and 30 are not particularly critical and can vary within fairly wide limits. In most cases, first panel 20 can possess an average thickness of from about 0.001 to about 0.01 inches, preferably from about 0.002 to about 0.008 inches, and most preferably, from about 0.004 to about 0.006 inches. Second panel 30 can possess an average thickness of from about 0.001 to about 0.008 inches and preferably from about 0.004 to about 0.006 inches including coatings and polymeric layers. Second panel 30 preferably includes at least one metal foil layer having a thickness of from about 0.0002 to about 0.0008 inches and preferably from about 0.0004 to about 0.0006 inches.

Figure 3:
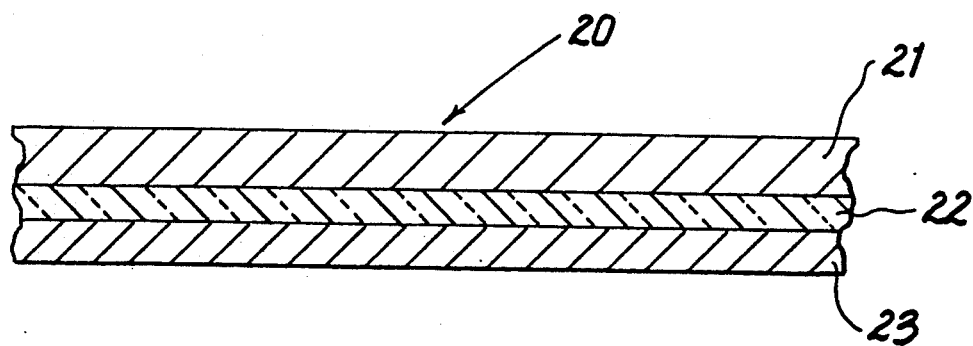
FIGS. 3 and 4 are, respectively, schematic cross-sectional views of the first and second panels of the flexible package of FIGS. 1 and 2 showing the details of their construction; and, FIG. 5 is a plan view, partly in section, of the desiccant unit present within the pouch of the sealed package of FIGS. 1 and 2.

First panel 20, shown in exaggerated cross sectional profile in FIG. 3, is preferably a transparent flexible laminate film possessing a polymeric base layer 21, an intermediate inorganic thin film layer 22 having a low moisture vapor transmission rate and a heat-sealable coating layer 23. First panel 20 can be constructed in accordance with any of the known transparent flexible laminate films possessing an inorganic moisture vapor transmission barrier layer, e.g., the laminate films described in aforementioned U.S. Pat. Nos. 3,442,686, 4,528,244, 4,702,963 and 5,084,356, the contents of which are incorporated by reference herein. Thus, e.g., polymeric base layer 21 can be formed from a polyester, advantageously polyethylene terephthalate, a polyamide, a polyolefin such as polyethylene, polypropylene, poly(ethylene-propylene) copolymer, a halopolymer resin such as polyvinyl chloride, polyvinyl fluoride, polyvinylidene chloride, polyvinylidene fluoride, polyimide, polycarbonate, polyurethane, polystyrene, hydrolyzed ethylene-vinyl acetate copolymer, a cellulosic resin such as regenerated cellulose (cellophane), cellulose acetate, etc. The base polymer layer can be used as is or subsequent to such known surface treating operations as exposure to chemical oxidizing agent or corona discharge, coating with a primer, etc., to improve its bond strength. The average thickness of polymeric base layer 21 can vary widely with thicknesses of from about 0.0005 to about 0.005 inches and preferably from about 0.0001 to about 0.003 inches generally providing good results.

Inorganic moisture vapor transmission barrier layer 22 is advantageously based on one or more oxides of silicon, aluminum, zirconium, etc., optionally containing a metal dopant for enhanced barrier properties as disclosed in U.S. Pat. No. 5,084,356, supra. Layer 22 is substantially continuous, i.e., unbroken, and can be formed upon polymeric base layer 21 employing any suitable technique, e.g., vacuum deposition or sputtering in an inert gas such as argon. The average thickness of barrier layer 22 is advantageously that which will provide a moisture vapor transmission rate (MVTR) not exceeding about 0.1 g/100 in$^2$/24 hrs., preferably not exceeding about 0.05 g/100 in$^2$/24 hrs. and more preferably not exceeding about 0.025 g/100 in$^2$/24 hrs. Generally, barrier layer thicknesses of from about 500 to about 5,000 Angstroms and preferably from about 100 to about 4,000 Angstroms are capable of providing such MVTRs. Optimum thicknesses of barrier layer 22 can, of course, be determined for particular requirements employing routine testing.

Heat sealable coating layer 23 is provided to enable bonding of the mutually contacting edges of panels 20 and 30 and the final sealing of the filled package by one or more seal strips, e.g., seals 27a and 27b of package 10. Heat sealable coating layer 23 can be formed from any of a variety of materials which are known to be suitable for this purpose including such water based adhesives as RP-1A of Rollprint Packaging Products, Inc., Addison, Ill. The average thickness of heat sealable coating layer 32 is not critical with thicknesses on the order of from about 0.0001 to about 0.001 inches and preferably from about 0.0002 to about 0.0005 inches being suitable in most cases. The provision of a heat sealable coating layer allows package 10 to be opened by peeling panels 20 and 30 apart, the panels separating at their heat sealed areas. Peelable packages are much preferred over tearable pouches which have often been used for packaging absorbable medical devices.

Figure 4:
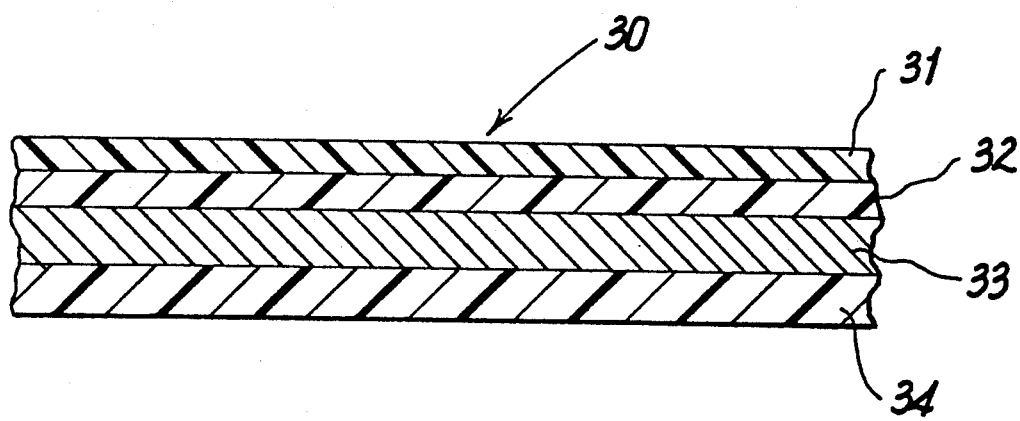

Second panel 30, shown in exaggerated cross sectional profile in FIG. 4, is an opaque, flexible metal foil laminate having no measurable moisture vapor transmission rate and is preferably an aluminum foil laminate numerous types of which are commercially available. Alternatively, second panel 30 can be fabricated from the same transparent flexible laminate film as first panel 20 to provide a totally transparent package. The laminate shown in FIG. 4 possesses a heat sealable coating layer 31, advantageously of a composition and a thickness corresponding to that of heat sealable coating layer 23 of first panel 20 described above, first and second polymeric layers 32 and 34, respectively, which can be the same or different resin and can be selected from among any of the polymers indicated above to be useful for polymer base layer 21 of panel 20, and an aluminum foil layer 33. Aluminum foil layer 33 possesses an average thickness of from about 0.0003 to about 0.001 inches and preferably from about 0.0004 to about 0.0006 inches and is coated or laminated on one side with first polymeric layer 32, advantageously having an average thickness of from about 0.0003 to about 0.0007 inches and preferably from about 0.0004 to about 0.0006 inches, and on the other side with second polymeric layer 34, advantageously having an average thickness of from about 0.001 to about 0.005 inches and preferably from about 0.002 to about 0.004 inches.

Package 10 of FIG. 1 contains at least one desiccant unit for absorbing moisture which may penetrate the package, particularly after prolonged periods of storage. Many suitable desiccant materials and desiccant arrangements are known, e.g., those described in aforementioned U.S. Pat. Nos. 3,301,788, 3,326,810 and 4,036,360, the contents of which are incorporated by reference herein. Particularly useful desiccant materials include molecular sieves, e.g., crystalline aluminosilicates such as zeolite Z-12, and silica gels. Desiccant unit 50 illustrated in FIG. 4 contains approximately 5 g of silica gel beads 51, optionally containing a small quantity of a moisture indicator such as cobalt chloride, in an inner flexible pouch 52 formed from two panels of a transparent laminate film heat sealed to each other along their edges. The laminate film of inner pouch 52 is made up of a layer of polyamide having a thickness of from about 0.0004 to about 0.0008 inches, preferably from about 0.0005 to about 0.0007 inches, and a layer of ethylene vinyl acetate having a thickness of from about 0.001 to about 0.004 inches and preferably from about 0.002 to about 0.003 inches. Pouch 52, in turn, is enclosed within an outer pouch 53 to contain the contents of inner pouch 52 should the latter break. Outer pouch is constructed from a transparent polyester film having an average thickness of about 0.001 inches and bonded along its edges to a spun-bonded polyethylene film such as Tyvek (Du Pont) of from about 0.005 to about 0.010 inches average thickness. The moisture vapor transmission rate of the material from which the desiccant pouch is made is on the order of from about 1 to about 1.5 g/100 in$^2$/24 hours.

In order to evaluate the effectiveness of the package of this invention for providing a stable environment for absorbable staples and clips, shelf-life tests were carried out upon sealed packages each of which contained a quantity of absorbable surgical staples or absorbable clips within the magazine of an applicator instrument together with differing numbers of desiccant units each containing 5 g silica gel desiccant. The absorbable surgical staples were made in accordance with U.S. Pat. Nos. 4,744,365, 4,844,854 and 4,839,130. The absorbable surgical clips were made in accordance with U.S. Pat. No. 4,523,591. The packages, which had pouch dimensions of approximately 13 by 5 inches, possessed, as first panel 20, a laminate itself made up of three 48 gauge laminates of Clearfoil ™ I (Rollprint Packaging Products, Inc., Addison, Ill.), each laminate layer possessing a polyethylene terephthalate base layer, a silicon oxide moisture vapor transmission barrier intermediate layer and a heat sealable top coating layer of RP-1A (Rollprint Packaging Products, Inc., Addison, Ill.), bonded at its edges to the edges of, as second panel 30, a four ply aluminum foil laminate possessing a polyester layer of 0.00048 inches thickness, a polyolefinamide layer of 0.0025 inches thickness, an aluminum foil layer of 0.005 inches thickness, a low density polyethylene layer of 0.003 inches thickness and a layer of RP1A heat sealable coating applied to the laminate at a rate of 3.5 pounds per ream (3,000 square feet).

Following 26 and 52 weeks (26W and 52W, respectively) exposure under both ambient (AMB) and elevated (33° C., 50% relative humidity) (ELEV) conditions, chemical and functional testing was carried out upon the clips and staples to determine whether they still met specifications. The physical/functional data for the clips and staples is set forth in Table 1.

TABLE 1

PHYSICAL/FUNCTIONAL DATA

| Package | Contents | Desiccant Pouches | Test | T-O | 26W AMB | 26W ELEV | 52W AMB | 52W ELEV | SPEC |
|---|---|---|---|---|---|---|---|---|---|
| 1 | clips | 1 | A | N/A | 0.003 | 0.0035 | 0.004 | 0.003 | .002–.006 |
|   |       |   | B | N/A | 1.48 | 1.59 | 1.95 | 2.16 | >0.79 |
|   |       |   | C | N/A | N/A | 1.4 | N/A | 1.31 | 1.15–1.50 |
| 2 | clips | 5 | A | N/A | 0.0029 | 0.0044 | 0.004 | 0.003 | .002–.006 |
|   |       |   | B | N/A | 1.46 | 1.13 | 1.86 | 1.92 | >0.79 |
|   |       |   | C | N/A | N/A | 1.4 | N/A | 1.32 | 1.15–1.50 |
| 3 | clips | 9 | A | N/A | 0.0026 | 0.0045 | 0.004 | 0.003 | .002–.006 |
|   |       |   | B | N/A | 1.4 | 1.35 | 1.87 | 2.21 | >0.79 |
|   |       |   | C | N/A | N/A | 1.43 | N/A | 1.3 | 1.15–1.50 |
| 4 | staples | 1 | C | N/A | N/A | 1.22 | N/A | 1.29 | 1.05–1.55 |
|   |       |   | B | 3.87 | 3.6 | 3.5 | 3.68 | 3.95 | 2.79 |
|   |       |   | D | 0.39 | 0.32 | 0.43 | 0.42 | 0.47 | <.45 |
| 5 | staples | 5 | C | N/A | N/A | 1.16 | N/A | 1.25 | 1.05–1.55 |
|   |       |   | B | 3.78 | 3.7 | 3.49 | 3.97 | 3.48 | >2.72 |
|   |       |   | D | 0.44 | 0.41 | 0.51 | 0.41 | 0.45 | <1.45 |
| 6 | staples | 9 | C | N/A | N/A | 1.25 | N/A | 1.24 | 1.05–1.55 |
|   |       |   | B | 3.21 | 3.77 | 3.43 | 3.78 | 3.99 | >2.72 |
|   |       |   | D | 0.41 | 0.34 | 0.35 | 0.32 | 0.38 | <.45 |

N/A = Not Applicable
Test A — gap, in
Test B — force to pull staple apart (out of package). KgF
Test C — inherent viscosity. decaliters per gram (as measured by a Schott Model AVS 500 Automatic Viscometer)
Test D — force to pull apart staples after 3 weeks in vitro (37° C.)

As shown in Table 1, the physical and chemical properties of the clips and staples inside the packages did not significantly change through the 26 and 52 weeks of exposure. In addition, qualitative evaluation indicated that the clips and staples satisfied functional requirements, particularly including clip closure and staple closure and formation. In the case of clips, clips were fired in air for observation of clip formation. In the case of absorbable staples, a line of staples was fired into foam sheeting to observe whether proper staple line formation was obtained. In all cases, proper clip and staple formation was observed.

We claim:

1. A flexible package which comprises a first panel fabricated from a substantially transparent flexible polymeric laminate film possessing an inorganic moisture vapor transmission barrier layer, said first panel having a measurable moisture vapor transmission rate, the first panel being bonded along its edges to the edges of a second panel fabricated from a material selected from the group consisting of (i) substantially transparent flexible polymeric laminate film possessing an inorganic moisture vapor transmission barrier layer which is the same as, or is different from, the film of the first panel and (ii) an opaque, flexible metal foil laminate, to form a contents-enclosing pouch therebetween, the pouch containing a quantity of desiccant and at least one sterile moisture-sensitive device or material, the desiccant being provided as at least one discrete desiccant unit loosely contained within the pouch or in a fixed location therein, the desiccant unit itself comprising a pouch made from a material having a moisture vapor transmission rate of about 1 g/100 in²/24 hrs with the desiccant contained within a pouch of the desiccant unit.

2. The package of claim 1 wherein at least said first panel transparent polymeric laminate film includes a layer formed from a polymer selected from the group consisting of polyester, polyamide, polyolefin, halopolymer, polyimide, polycarbonate, polyurethane, polystyrene, hydrolyzed ethylene-vinyl acetate copolymer and cellulosic resin.

3. The package of claim 1 wherein at least said first panel transparent polymeric laminate film includes a layer formed from polyethylene terephthalate.

4. The package of claim 1 wherein the inorganic moisture vapor transmission barrier layer is formed from at least one oxide selected from the group consisting of silicon oxide, aluminum oxide and zirconium oxide.

5. The package of claim 1 wherein the inorganic moisture vapor transmission barrier layer is formed from at least one oxide of silicon, aluminum and zirconium containing a metal dopant.

6. The package of claim 1 wherein the second panel is fabricated from an aluminum foil laminate.

7. The package of claim 1 wherein the second panel is fabricated from an aluminum foil laminate possessing a low density polyethylene layer on one side and a polyamide layer on the other.

8. The package of claim 1 wherein the moisture vapor transmission rate of the inorganic moisture vapor transmission barrier layer does not exceed about 0.1 g/100 in²/24 hrs.

9. The package of claim 1 wherein the moisture vapor transmission rate of the inorganic moisture vapor transmission barrier layer does not exceed about 0.05 g/100 in²/24 hrs.

10. The package of claim 1, wherein the moisture vapor transmission rate of the inorganic moisture vapor transmission barrier layer does not exceed about 0.025 g/100 in²/24 hrs.

11. The package of claim 1 wherein the desiccant is at least one material selected from the group consisting of silica gel and molecular sieve.

12. The package of claim 1 wherein the desiccant includes a material which indicates by change of color when the capacity of the desiccant for absorbing moisture has been effectively exhausted.

13. The package of claim 1, wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate and the desiccant unit contains at least one desiccant material selected from the group consisting of silica gel and molecular sieve.

14. The package of claim 1 wherein the first panel is bonded to the second panel through a heat sealable coating composition applied to one or both mutually contacting surfaces of the panels.

15. The package of claim 1, wherein the first panel is peelable from the second panel.

16. The package of claim 1 wherein the moisture sensitive device is a bioabsorbable hemostatic or wound closure device.

17. The package of claim 1 wherein the moisture sensitive device is a bioabsorbable clip or staple.

18. The package of claim 1 wherein the moisture sensitive device is a bioabsorbable clip or staple stored within an apparatus for applying the clip or staple.

19. The package of claim 1 wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate, the desiccant unit contains at least one desiccant material selected from the group consisting of silica gel and molecular sieve and the moisture-sensitive device is a bioabsorbable hemostatic or wound closure device.

20. A flexible package which comprises a first panel fabricated from a substantially transparent flexible polymeric laminate film possessing an inorganic moisture vapor transmission barrier layer, said first panel having a measurable moisture vapor transmission rate, the first panel being bonded along its edges to the edges of a second panel fabricated from a material selected from the group consisting of (i) substantially transparent flexible polymeric laminate film possessing an inorganic moisture vapor transmission barrier layer which is the same as, or is different from, the film of the first panel and (ii) an opaque, flexible metal foil laminate, to form a contents-enclosing pouch therebetween, the pouch containing a quantity of desiccant and at least one sterile moisture-sensitive device or material, and a removable header at least partially fabricated from a gas permeable sheet material which is a barrier to microorganisms, one end of the header being attached to the opening of the package and the other end of the header being open or sealed.

21. The package of claim 20 wherein the gas permeable sheet of the header is a spunbonded polyethylene.

22. The package of claim 20 from which the header has been removed with the exception of a residual strip of header material.

23. The package of claim 20 wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate, the desiccant unit contains at least one desiccant material selected from the group consisting of silica gel and molecular sieve and the moisture-sensitive device is a bioabsorbable hemostatic or wound closure device.

24. A method of packaging a moisture-sensitive device or material which comprises:
   a) providing an open flexible package comprising a first panel fabricated from a substantially transparent flexible polymeric laminate film possessing an inorganic moisture vapor transmission barrier layer, the first panel being bonded along its edges to the edges of a second panel fabricated from a material selected from the group consisting of (i) a substantially transparent flexible polymeric laminate film possessing an inorganic moisture vapor transmission barrier layer which is the same as, or is different from, the film of the first panel and (ii) an opaque, flexible metal foil laminate, to form a contents-receiving open pouch therebetween;
   b) placing at least one moisture-sensitive device or material and a quantity of desiccant within the pouch, the desiccant being provided as at least one discrete desiccant unit loosely contained within the pouch or in a fixed location therein, the desiccant unit itself comprising a pouch made from a material having a moisture vapor transmission rate of about 1 g/100 /in$^2$/24 hrs with the desiccant contained within a pouch of the desiccant unit;
   c) sealing the pouch; and,
   d) sterilizing the contents of the package.

25. The method of claim 24 wherein at least said first transparent polymeric laminate film includes a layer formed from a polymer selected from the group consisting of polyester, polyamide, polyolefin, halopolymer, polyimide, polycarbonate, polyurethane, polystyrene, hydrolyzed ethylene-vinyl acetate copolymer and cellulosic resin.

26. The method of claim 24 wherein at least said first transparent polymeric laminate film includes a layer formed from polyethylene terephthalate.

27. The method of claim 24 wherein the inorganic moisture vapor transmission barrier layer is formed from at least one oxide selected from the group consisting of silicon oxide, aluminum oxide and zirconium oxide.

28. The method of claim 24 wherein the inorganic moisture vapor transmission barrier layer is formed from at least one oxide of silicon, aluminum and zirconium containing a metal dopant.

29. The method of claim 24 wherein the second panel is fabricated from an aluminum foil laminate.

30. The method of claim 24 wherein the second panel is fabricated from an aluminum foil laminate possessing a low density polyethylene layer on one side and a polyamide layer on the other.

31. The method of claim 24 wherein the moisture vapor transmission rate of the inorganic moisture vapor transmission barrier layer does not exceed about 0.1 g/100 in$^2$/24 hrs.

32. The method of claim 24 wherein the moisture vapor transmission rate of the inorganic moisture vapor transmission barrier layer does not exceed about 0.05 g/100 in$^2$/24 hrs.

33. The method of claim 24 wherein the moisture vapor transmission rate of the inorganic moisture vapor transmission barrier layer does not exceed about 0.025 g/100 in$^2$/24 hrs.

34. The method of claim 24 wherein the desiccant is at least one material selected from the group consisting of silica gel and molecular sieve.

35. The method of claim 24 wherein the desiccant includes a material which indicated by change of color when the capacity of the desiccant for absorbing moisture has been effectively exhausted.

36. The method of claim 24 wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate, the desiccant unit contains at least one desiccant material selected from the group consisting of silica gel and molecular sieve and the moisture-sensitive device is a bioabsorbable hemostatic or wound closure device.

37. The method of claim 24 wherein the first panel is bonded to the second panel through a heat sealable coating composition applied to one or both mutually containing surfaces of the panels.

38. The method of claim 24 wherein the first panel is peelable from the second panel.

39. The method of claim 24 wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate, the desiccant unit contains at least one desiccant material selected from the group consisting of silica gel and molecular sieve and the moisture-sensitive device is a bioabsorbable hemostatic or wound closure device.

40. A method of packaging a moisture-sensitive device or material which comprises:
 a) providing an open flexible package comprising a first panel fabricated from a substantially transparent flexible polymeric laminate film possessing an inorganic moisture vapor transmission barrier layer, the first panel being bonded along its edges to the edges of a second panel fabricated from a material selected from the group consisting of (i) a substantially transparent flexible polymeric film possessing an inorganic moisture vapor transmission barrier layer which is the same as, or is different from, the film of the first panel and (ii) an opaque, flexible metal foil laminate, to form a contents-receiving open pouch therebetween, and a header at least partially fabricated from a gas permeable sheet material which is a barrier to microorganisms, one end of the header being attached to the opening of the package and the other end of the header being open;
 b) placing at least one moisture-sensitive device or material and a quantity of desiccant within the open pouch;
 c) sealing the open end of the header;
 d) introducing a sterilizing gas into the pouch through the gas permeable sheet of the header to sterilize the contents of the package;
 e) removing the sterilizing gas from the pouch following sterilization of its contents;
 f) sealing the package; and,
 g) removing at least part of the header.

41. The method of claim 40 wherein the gas permeable sheet of the header is a spunbonded polyethylene.

42. The method of claim 40 wherein at least said first panel transparent polymeric laminate film includes a layer formed from a polymer selected from the group consisting of polyester, polyamide, polyolefin, halogenated polymer, polyimide, polycarbonate, polyurethane, polystyrene, hydrolyzed ethylene-vinyl acetate copolymer and cellulosic resin, the inorganic moisture vapor transmission barrier layer is formed from at least one oxide selected from the group consisting of silicon oxide, aluminum oxide and zirconium oxide, the metal foil laminate is an aluminum foil laminate, the desiccant unit contains at least one desiccant material selected from the group consisting of silica gel and molecular sieve and the moisture-sensitive device is a bioabsorbable hemostatic or wound closure device.

* * * * *